US009193686B2

(12) United States Patent
Gollut et al.

(10) Patent No.: US 9,193,686 B2
(45) Date of Patent: Nov. 24, 2015

(54) PROCESS FOR THE PREPARATION OF A QUINOLINE CARBOXYLIC ACID

(71) Applicant: Syngenta Participations AG, Basel (CH)

(72) Inventors: Jean-Jacques Roger Gollut, Monthey (CH); Arnaud Jean Albert Gayet, Monthey (CH)

(73) Assignee: Syngenta Participations AG, Basel (CH)

( * ) Notice: Subject to any disclaimer, the term of this patent is extended or adjusted under 35 U.S.C. 154(b) by 44 days.

(21) Appl. No.: 14/357,254

(22) PCT Filed: Nov. 14, 2012

(86) PCT No.: PCT/EP2012/072636
§ 371 (c)(1),
(2) Date: May 9, 2014

(87) PCT Pub. No.: WO2013/072376
PCT Pub. Date: May 23, 2013

(65) Prior Publication Data
US 2014/0323302 A1 Oct. 30, 2014

(30) Foreign Application Priority Data
Nov. 14, 2011 (GB) .................................. 1119690.4

(51) Int. Cl.
*C07D 215/26* (2006.01)
*C07D 215/04* (2006.01)
(Continued)

(52) U.S. Cl.
CPC .............. *C07D 215/26* (2013.01); *A01N 25/32* (2013.01); *C07D 215/04* (2013.01); *C07D 215/10* (2013.01); *Y10T 428/2982* (2015.01)

(58) Field of Classification Search
CPC .. C07D 215/04; C07D 215/10; C07D 215/26; C07D 215/28; A01N 25/32; A01N 43/42; Y10T 428/2982
See application file for complete search history.

(56) References Cited

U.S. PATENT DOCUMENTS 3,351,525 A * 11/1967 Hodel .................. A23K 1/1625
514/235.2
5,441,922 A * 8/1995 Ort ........................ A01N 25/32
504/104

FOREIGN PATENT DOCUMENTS

EP 0094349 A2 * 5/1983 ........... C07D 215/26
GB 2120661 12/1983
(Continued)

OTHER PUBLICATIONS

Morgun et al., "Synthesis of quinolyloxyaceticacids", DopovidiL'viv'sk. Derzh. Univ., vol. 9, part 2, 1961, pp. 75-77.*
(Continued)

*Primary Examiner* — Jane C Oswecki
(74) *Attorney, Agent, or Firm* — R. Kody Jones

(57) ABSTRACT

The invention provides a process for the preparation of a carboxylic acid of formula (IV) (which is useful as a safener for herbicides): wherein $R_1$ is hydrogen or chlorine, comprising the steps of: (i) subjecting a compound of formula (V) wherein: $R_1$ is as defined above; and $R_2$ is $C_1$-$C_{18}$ alkyl; $C_1$-$C_6$ alkoxy$C_1$-$C_8$ alkyl-; optionally substituted phenyl; or optionally substituted benzyl; to hydrolysis under acidic conditions to give a solution of a quinolinium salt; and (ii) adding base to the solution obtained in step (i) to give the free carboxylic acid (IV). The invention also provides a solid (e.g. particulate) form of one quinoline carboxylic acid compound within formula (IV) defined by $R_1$ being chlorine; and novel intermediates useable in the above process.

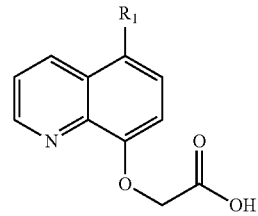

(IV)

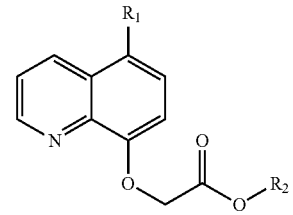

(V)

17 Claims, 1 Drawing Sheet

(51) Int. Cl.
*C07D 215/10* (2006.01)
*A01N 25/32* (2006.01)
*C07D 215/28* (2006.01)

(56) References Cited

FOREIGN PATENT DOCUMENTS

| GB | 2120661 A | * | 12/1983 | ............ | C07D 215/24 |
| WO | 0200625 | | 1/2002 | | |
| WO | WO02/00625 A2 | * | 1/2002 | ............ | C07D 215/28 |

OTHER PUBLICATIONS

Moszew et al., "Synthesis of several isomeric quinolineacetic acids", Roczniki Chemii, 1959, vol. 33, pp. 365-370.*
Interntaional Search Report dated Jan. 30, 2013 for International Patent Application No. PCT/EP2012/072636.
UK IPO Search Report dated Mar. 1, 2012 for GB 1119690.4.
Morgun et al., "Synthesis of quinolyloxyaceticacids," See CAS abstract Accession No. 1963: 428460; Dopovidi L'viv'sk. Derzh. Univ., vol. 9, part 2, 1961, pp. 75-77.
Moszew et al., "Synthesis of several isomeric quinolineacetic acids," Roczniki Chemii, vol. 33, 1959, pp. 365-370, See CAS abstract Accession No. 1959:122160.

* cited by examiner

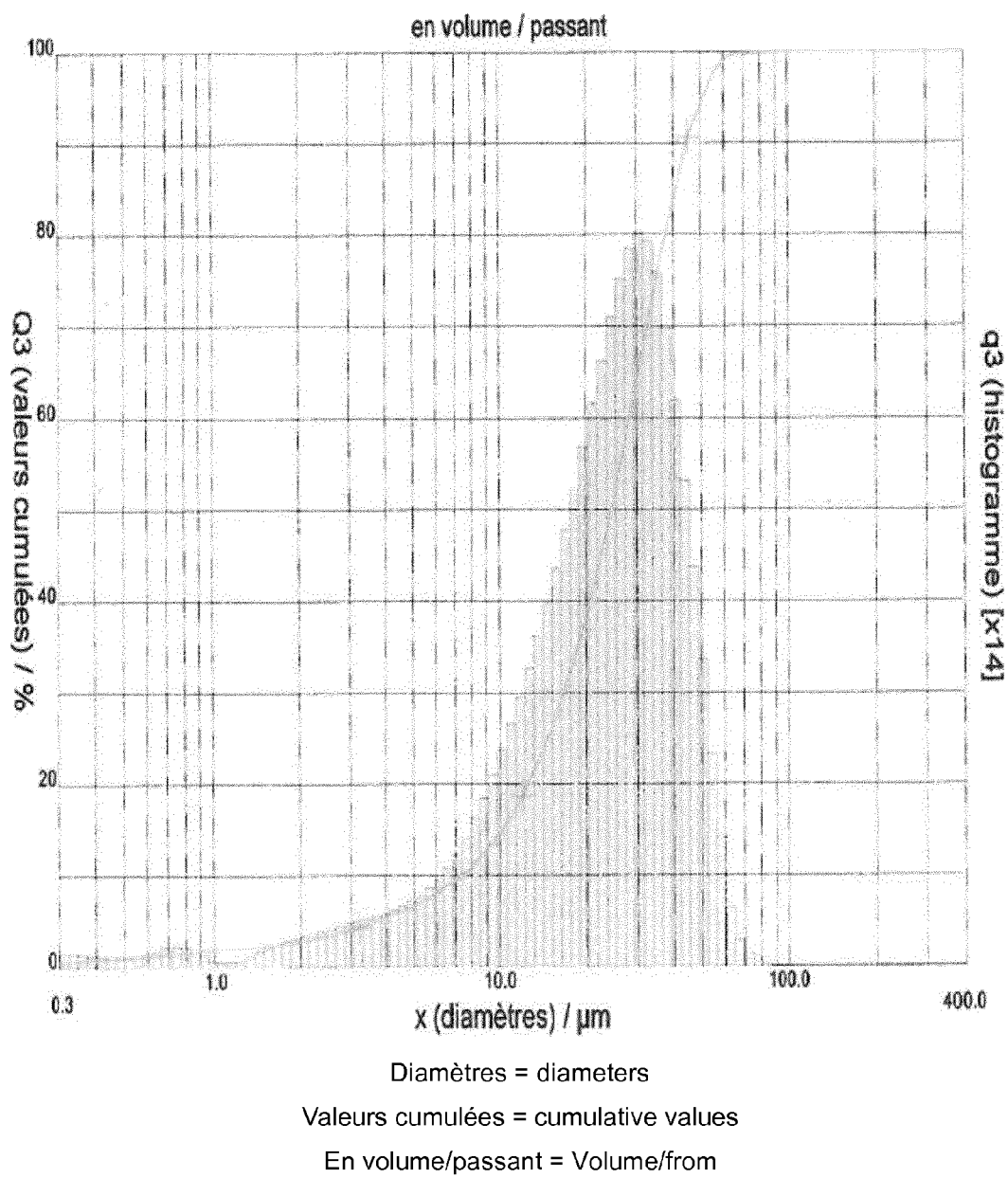
Diamètres = diameters
Valeurs cumulées = cumulative values
En volume/passant = Volume/from
histogramme = histogram

PROCESS FOR THE PREPARATION OF A QUINOLINE CARBOXYLIC ACID

RELATED APPLICATION INFORMATION

This application is a 371 of International Application No. PCT/EP2012/072636, filed 14 Nov. 2012, which claims priority to GB Patent Application No. 1119690.4, filed 14 Nov. 2011, the contents of which are incorporated herein by reference herein.

The present invention relates to a process for the preparation of a quinoline carboxylic acid (e.g. cloquintocet acid), more specifically to a process for the preparation of a quinoline carboxylic acid (e.g. cloquintocet acid) by the hydrolysis of an ester thereof, a composition obtained(able) by such a process, an intermediate useful in such a process, and a solid form of the quinoline carboxylic acid (e.g. cloquintocet acid) capable of being prepared by the process.

BACKGROUND TO THE INVENTION

Quinoline derivatives useful for protecting cultivated plants from the phytotoxic action of herbicides (i.e. useful as "safeners") are known, for example, from EP-A-0 094 349, U.S. Pat. No. 5,102,445 and U.S. Pat. No. 5,441,922.

According to U.S. Pat. No. 5,102,445, such quinoline derivatives, in particular an alkyl (8-quinolinoxy)-acetate or an alkyl 2-(8-quinolinoxy)-propionate or a ring-substituted derivative of either of these, can be prepared inter alia by reacting 8-hydroxyquinoline or a ring-substituted derivative thereof with a haloacetic acid derivative (such as an alkyl haloacetate, e.g. an alkyl chloroacetate) or a 2-halo-propionic acid derivative (such as an alkyl 2-halo-propionate, e.g. methyl 2-bromo-propionate), typically in the presence of a base (e.g. potassium carbonate) in an inert solvent (e.g. butan-2-one) at elevated temperature, preferably in the presence of a catalytic amount of alkali metal iodide. See columns 2, 17, 21, 22 and 23-24 (Example 1) in U.S. Pat. No. 5,102,445. The yields obtained are often not very satisfactory, especially for the large-scale preparation of those compounds. Furthermore, undesirable by-products, e.g. alcohols, which can significantly reduce product quality, can be formed in that process.

Cloquintocet-mexyl is commercially used as a safener of herbicides (specifically, the grass-active herbicides clodinafop-propargyl or pinoxaden, or the herbicide pyroxsulam, or the herbicide flucarbazone or a salt (e.g. sodium salt) thereof) in small grain cereal crops such as wheat (see, e.g., The Pesticide Manual, 15th edition, 2009, British Crop Production Council, entry 174, pages 226-227). It accelerates the detoxification process of clodinafop-propargyl in cereals e.g. wheat (Kreuz et al., Z. Naturforsch., 1991, 46c, pp. 901-905). The IUPAC chemical name of cloquintocet-mexyl is 1-methylhexyl (5-chloroquinolin-8-yloxy)acetate, and its chemical structure is:

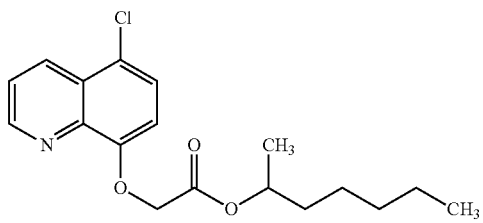 [SMILES: CCCCCC(C)OC(=O)COc1ccc(Cl)c2cccnc12]

The free acid (ester-free) derivative of cloquintocet-mexyl, (5-chloroquinolin-8-yloxy)acetic acid ("cloquintocet acid"), is also thought to be useful as a herbicide safener, e.g. as a safener for clodinafop-propargyl, pinoxaden, flucarbazone or a salt (e.g. sodium salt) thereof, or, in particular, pyroxsulam. Cloquintocet acid has the following structure:

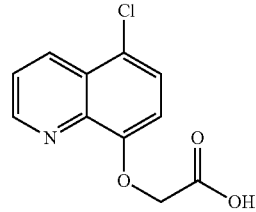 [SMILES: O=C(O)COc1ccc(Cl)c2cccnc12]

WO 02/00625 A discloses a process for the preparation of a compound of formula (I)

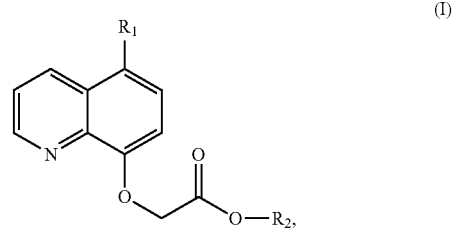

wherein $R_1$ is hydrogen or chlorine, and $R_2$ is hydrogen, $C_1$-$C_8$ alkyl, or $C_1$-$C_8$ alkyl substituted by $C_1$-$C_6$ alkoxy or by $C_3$-$C_6$ alkenyloxy, which process comprises a) introducing the major portion of the amount to be reacted of a compound of formula (II)

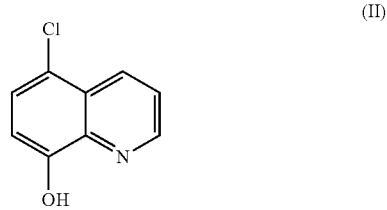 [SMILES: Oc1ccc(Cl)c2cccnc12]

into a solvent mixture comprising at least one organic solvent capable of forming an azeotrope with water, and at least one aprotic-dipolar solvent; b) metering in an aqueous strong base (preferably an alkali metal hydroxide, e.g. NaOH or KOH, or an alkaline earth metal hydroxide) in an amount equivalent to that major portion of the total amount of the compound of formula (II); c) adding the remaining portion of the amount to be reacted of the compound of formula (II); d) adding a weak base (preferably an alkali metal carbonate, e.g. $Na_2CO_3$ or $K_2CO_3$, or an alkaline earth metal carbonate) in an amount that is at least equivalent to that remaining portion; e) removing the water from the reaction mixture by azeotropic distillation; f) adding a compound of formula (III)

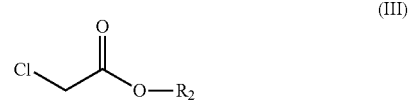

wherein $R_2$ is as defined for formula (I); and g) isolating the resulting compound of formula (I) from the reaction mixture.

This WO 02/00625 A process is good, but is not perfect for preparation of compounds of formula (I) wherein $R_2$ is hydrogen, as the chloroacetic acid starting material (III, $R_2$=H) forms a salt under the basic reaction conditions used.

The aim of the present invention is accordingly to provide a process for the preparation of non-ester quinoline carboxylic acids, specifically (5-chloroquinolin-8-yloxy)acetic acid ("cloquintocet acid", which is useful as a herbicide safener) or (quinolin-8-yloxy)acetic acid, that is distinguished by high yields and/or good product quality and/or that avoids one or more possible disadvantages of alternative processes.

SUMMARY OF THE INVENTION

According to a first aspect of the invention, there is provided a process for the preparation of a carboxylic acid of formula (IV)

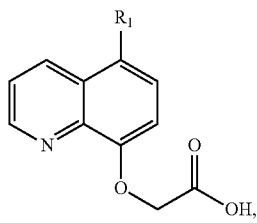

(IV)

wherein $R_1$ is hydrogen or chlorine,
comprising the steps of:
(i) subjecting a compound of formula (V)

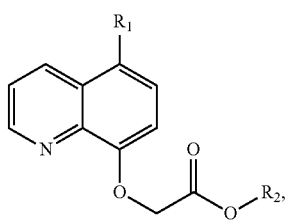

(V)

wherein: $R_1$ is as defined above; and $R_2$ is $C_1$-$C_{18}$alkyl; $C_1$-$C_6$alkoxy$C_1$-$C_8$alkyl-; or phenyl or benzyl, wherein the phenyl or benzyl is optionally substituted on the ring by 1, 2 or 3 of independently fluorine, chlorine, $C_1$-$C_2$alkyl, $C_1$-$C_2$alkoxy, $C_1$fluoroalkyl, or $C_1$fluoroalkoxy;
to hydrolysis under acidic conditions to give a solution of a quinolinium salt whose cation is of formula (VI)

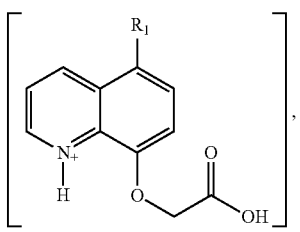

(VI)

wherein $R_1$ is as defined above; and
(ii) adding base to the solution obtained in step (i) to give the free carboxylic acid (IV).

In a second aspect, the invention relates to a compound of the formula

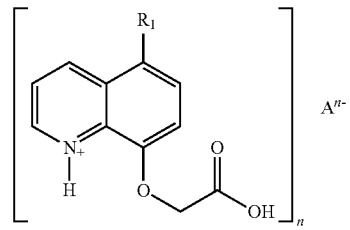

wherein n is 1, 2 or 3, $R_1$ is as defined herein, and $A^{n-}$ is an n valent anion. This can be used an intermediate in a process for the preparation of the compound (IV).

In a third aspect, the invention relates to carboxylic acid (IV) (preferably particulate) having a specific particle size distribution.

SUMMARY OF THE FIGURES

FIG. 1 is a histogram showing the particle size distribution of cloquintocet acid obtained by a process according to the invention.

DETAILED DESCRIPTION OF THE PREFERRED EMBODIMENTS

Alkyl, or a derivative of alkyl (e.g. alkoxy, alkoxyalkyl-, et al.), includes branched or straight-chain versions of alkyl or the derivative thereof.

$C_1$fluoroalkyl can be $CF_3$, $CHF_2$ or $CH_2F$. $C_1$fluoroalkoxy can be $CF_3O$, $CHF_2O$ or $CH_2FO$.

It is strongly preferred that $R_1$ is chlorine.

Preferably, $R_2$ is branched or straight-chain $C_1$-$C_{18}$ alkyl, or branched or straight-chain $C_1$-$C_6$alkoxy$C_1$-$C_8$alkyl-.

More preferably, $R_2$ is straight-chain $C_1$-$C_{10}$ alkyl or non-tertiary branched $C_3$-$C_{10}$ alkyl (e.g. straight-chain $C_1$-$C_8$ alkyl or non-tertiary branched $C_3$-$C_8$ alkyl); still more preferably straight-chain $C_1$-$C_{10}$ alkyl or —CH(Me)$C_1$-$C_8$alkyl (e.g. straight-chain $C_1$-$C_8$ alkyl or —CH(Me)$C_1$-$C_6$alkyl); such as methyl, ethyl, n-propyl, isopropyl, n-butyl, sec-butyl, isobutyl, n-pentyl, 1-methylbutyl, n-hexyl, 1-methylpentyl, n-heptyl, 1-methylhexyl, n-octyl or 1-methylheptyl. Especially preferably, $R_2$ is methyl, ethyl or 1-methylhexyl.

Most preferably, $R_2$ is 1-methylhexyl.

Compound (V) can be obtained using any method known in the art. For example, the processes used in WO02/00625A (e.g. as described hereinabove), U.S. Pat. No. 5,102,445 and U.S. Pat. No. 5,441,922 may be employed to prepare compound (V).

In a preferred embodiment, compound (V) is prepared by deprotonation of an 8-hydroxyquinoline (VII) with base, (suitably sodium hydroxide/potassium carbonate in N-methypyrrolidone) and reaction of anion (VIII) with a chloroacetic ester (IX) (Scheme 1):

Scheme 1

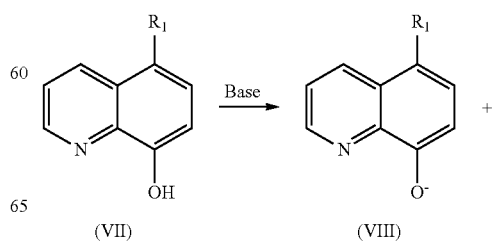

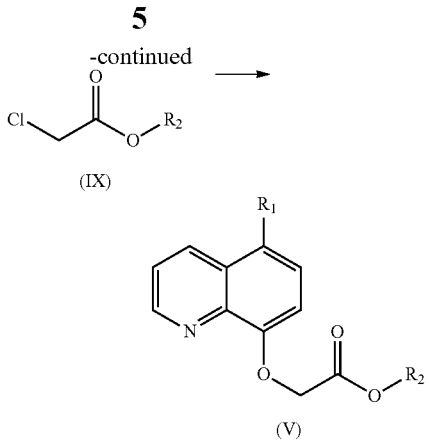

In the process for the preparation of the carboxylic acid of formula (IV), the acid hydrolysis step (i) is preferably carried out under aqueous conditions. Optionally, a co-solvent may be present, preferably a water-miscible aqueous co-solvent, such as a $C_1$-$C_6$ alcohol (e.g. $C_1$-$C_4$ or $C_1$-$C_3$ alcohol such as methanol, ethanol, n-propanol and/or isopropanol), dimethylsulfoxide, dimethylformamide or N-methylpyrrolidone.

Preferably, the acid for use in the hydrolysis step (i) is an organic or mineral acid, preferably a mineral acid. Preferably, the acid (e.g. for use in the hydrolysis step (i)) has a $pK_a$ of less than 4, more preferably, less than 1. Preferred mineral acids are selected from the group consisting of phosphoric, nitric, sulphuric, hydrohalic (e.g. hydrochloric, hydrobromic, or hydroiodic), and perchloric acid; and more preferably are selected from the group consisting of phosphoric, nitric, sulphuric, hydrochloric, and perchloric acid; most preferably hydrochloric acid. Preferred organic acids are selected from the group consisting of arylsulfonic acids, alkylsulfonic acids, fluoroalkylsulfonic acids and fluoroalkylcarboxylic acids, more preferably p-toluenesulfonic acid, a monobromobenzenesulfonic acid (e.g. 4-bromobenzenesulfonic acid), methanesulfonic acid, trifluoromethanesulfonic acid, trifluoroacetic acid and difluoroacetic acid.

The skilled person will appreciate that the quinolinium salt whose cation is of formula (VI), e.g. in the hydrolysis step (i), will have a counterbalancing anion such as $A^{n-}$ which is an n valent anion. The nature of anion $A^{n-}$ will in general depend of the nature of the acid used in the hydrolysis step (i), and in general will comprise the deprotonated anion(s) of the acid(s) used in the hydrolysis step (i). In particular, the anion $A^{n-}$ can be $PO_4^{3-}$, $NO_3^-$, $SO_4^{2-}$, perchlorate$^-$, halide$^-$ (the halide$^-$ can e.g. be Br$^-$, I$^-$, and/or Cl$^-$), p-toluenesulfonate, a monobromobenzenesulfonate (e.g. 4-bromobenzenesulfonate), methanesulfonate, trifluoromethanesulfonate, trifluoroacetate, and/or difluoroacetate. Preferably, the anion $A^{n-}$ is $PO_4^{3-}$, $NO_3^-$, $SO_4^{2-}$, and/or Cl$^-$, or most preferably Cl$^-$ (chloride anion) (e.g. with HCl-mediated hydrolysis).

Therefore, preferably, the quinolinium salt whose cation is of formula (VI), e.g. in the hydrolysis step (i), is a compound of the formula

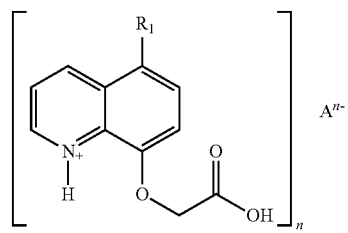

wherein n is 1, 2 or 3, $R_1$ is as defined herein, and $A^{n-}$ is an n valent anion. Preferably, $A^{n-}$ is $PO_4^{3-}$, $NO_3^-$, $SO_4^{2-}$, perchlorate$^-$, halide$^-$ (the halide$^-$ can e.g. be Br$^-$, I$^-$, and/or Cl$^-$), p-toluenesulfonate, a monobromobenzenesulfonate (e.g. 4-bromobenzenesulfonate), methanesulfonate, trifluoromethanesulfonate, trifluoroacetate, and/or difluoroacetate. More preferably, $A^{n-}$ is $PO_4^{3-}$, $NO_3^-$, $SO_4^{2-}$, and/or Cl$^-$. (The quinolinium salt compound having the above-shown formula also forms a second independent aspect of the invention.)

In the first aspect of the invention, preferably, the concentration of the acid is between 0.01 M and 10 M, more preferably between 0.1 M and 5 M, still more preferably between 0.5 M and 2 M.

In the first aspect of the invention, preferably, the concentration of the ester (V) is between 0.01 M and 10 M, more preferably between 0.1 M and 5 M, still more preferably between 0.5 M and 2 M.

The reaction, in particular in the hydrolysis step (i), is typically conducted at a temperature suitable for achieving an acceptable rate of reaction. Suitable temperatures range from 10 to 200° C., preferably from 20 to 150° C., more preferably from 50 to 120° C., still more preferably from 75 to 110° C. or from 85 to 105° C., yet more preferably about 100° C. Most preferably, the reaction is conducted at the reflux temperature of the solvent.

Optionally and preferably, $R_2OH$ (an alcohol, which is produced as a by-product in hydrolysis step (i)) is continuously removed from the reaction mixture during the course of the reaction. Several methods are of utility in this respect, typically sequestration of the alcohol with molecular sieves, distillation (e.g. azeotropic distillation), or physical entrainment, with distillation (e.g. azeotropic distillation) or physical entrainment being preferred.

During the hydrolysis step (i), the reaction mixture may be subject to agitation, such as by mechanical stirring. Additionally, the mixture may be protected from the atmosphere by means of a blanket of inert gas, such as nitrogen, argon or carbon dioxide.

At the conclusion of the acid hydrolysis step (i), a solution of the quinolinium salt whose cation is of formula (VI) is obtained. Preferably, in order to keep this salt (VI) in solution, the temperature is maintained at above ambient temperature, such as above 20, 30, 40, 50, 60, 70, 80 or 90° C.

The desired product (IV) is liberated from the solution of salt (VI) by addition of base (step (ii)). Suitable bases include inorganic bases, preferably selected from the group consisting of ammonia, metal hydroxides, metal carbonates, metal bicarbonates and metal oxides, and organic bases, preferably selected from the group consisting of mono-, di- or trialkylamines and pyridine derivatives. Preferably, the base comprises (or, alternatively, consists essentially of) a group (I) or group (II) metal hydroxide or carbonate, more preferably a group (I) hydroxide, still more preferably lithium hydroxide, sodium hydroxide or potassium hydroxide, e.g. sodium hydroxide or potassium hydroxide. Sodium hydroxide is the most preferred base.

Preferably, the base is provided as a solution, preferably an aqueous solution; more preferably aqueous lithium hydroxide, aqueous sodium hydroxide or aqueous potassium hydroxide, most preferably aqueous sodium hydroxide. The concentration of base is typically from 0.01 M to 13 M, preferably 0.1 M to 10 M, preferably 0.1 M to 5 M, more preferably 0.5 M to 1 M.

The desired carboxylic acid (IV) precipitates from the reaction mixture as the base is added. Preferably, the base is added over a period of between 15 and 480 minutes. More preferably, the base is added over a period of between 30 and 240 minutes. Still more preferably, the base is added over a period of between 60 and 180 minutes. Most preferably, the base is added over a period of about 120 minutes. This ensures that the precipitated acid has the physical form, and in particular a particle size distribution, appropriate for the subsequent uses of (IV), namely formulation as a herbicide safener or as a starting material in subsequent transformations.

Preferably, during addition of the base, a solution of the quinolinium salt whose cation is of formula (VI) obtained in step (i) is maintained at a temperature sufficient to prevent precipitation of (VI), preferably above ambient temperature, in particular above 20, 30, 40, 50, 60, 70, 80 or 90° C. If the base is in solution form, this may also be at an elevated temperature, such as above 20, 30, 40, 50, 60, 70, 80 or 90° C.; however, it is also possible to add base at ambient temperature (e.g. ca. 18-22° C.).

According to a highly preferred embodiment of the invention, it has been found that in order to obtain optimum yield of (IV), as well as to ensure good product purity, it is important to control the pH, e.g. of the solution or reaction mixture, during addition of the base in step (ii).

Preferably, the pH at the end of the base addition step (ii) is in the range of 1.8 to 3.8. That is, in the process, preferably the base in step (ii) is added until a pH in the range of 1.8 to 3.8 is achieved. More preferably, the pH at the end of the base addition step (ii) is in the range of 2.3 to 3.3. Still more preferably, the pH is in the range of 2.5 to 3.1. Still more preferably, the pH is in the range of 2.7 to 2.9. Most preferably, the pH is about 2.8.

According to a further aspect of the invention, there is provided a composition consisting essentially of carboxylic acid (IV) together with trace amounts of the sodium salt of (IV), the hydrochloride salt of (IV), 8-hydroxyquinoline (VII), potassium chloride and sodium chloride.

In the first aspect of the invention, the solution of quinolinium salt whose cation is of formula (VI) may be agitated during addition of the base, such as by mechanical stirring. Further, the solution of (VI) may be protected from the atmosphere, by the use of a blanket of inert gas, preferably nitrogen, argon or carbon dioxide.

Optionally and preferably, after the addition of the base to the solution of (VI) is complete, the suspension of carboxylic acid (IV) is allowed to cool.

After addition of the base and precipitation of carboxylic acid (IV), the carboxylic acid (IV) may be recovered (e.g. isolated) from the reaction mixture. Recovery (e.g. isolation) may conveniently be effected by filtration. Alternatively, the suspension of carboxylic acid (IV) may be used directly in subsequent process steps, or formulated directly into a plant protection product.

The carboxylic acid (IV) may be purified by any conventional means. Steps of drying, washing, trituration or recrystallization or any combination thereof may be involved. However, one of the advantages of the process of the present invention is that acid (IV) is obtained in a high degree of purity, and does not require further purification.

The carboxylic acid (IV) (e.g. particulate carboxylic acid of formula (IVa) shown hereinbelow), e.g. obtained by means of the process of the reaction, may be formulated as a plant protection product, e.g. together with any adjuvant(s) and/or excipient(s) (e.g. those which are conventional and/or known in the art). In particular, the carboxylic acid (IV) may be formulated together with a herbicide. [Therefore, another aspect of the invention provides a plant protection product formulation comprising a carboxylic acid of formula (IV) (e.g. a particulate carboxylic acid of formula (IVa) shown hereinbelow) formulated together with a herbicide, and optionally formulated together with adjuvant(s) and/or excipient(s).] Preferred herbicides are selected from the group consisting of:

pyridine herbicides;
sulfonamide herbicides (e.g. pyroxsulam or a salt (e.g. sodium salt) thereof);
triazolopyrimidine herbicides (e.g. pyroxsulam or a salt (e.g. sodium salt) thereof);
sulfonylamino-carbonyl-triazolinone herbicides (such as flucarbazone or propoxycarbazone or thiencarbazone-methyl or a salt (e.g. sodium salt) of any of these);
sulfonyl urea herbicides (e.g. mesosulfuron-methyl, iodosulfuron-methyl, bensulfuron-methyl, triasulfuron, or sulfosulfuron, or a salt (e.g. sodium salt) of any of these);
aryloxyphenoxypropionic herbicides (which group includes heteroaryloxyphenoxypropionic herbicides) (e.g. clodinafop, clodinafop-propargyl, fenoxaprop, fenoxaprop-P-ethyl, or diclofop-methyl);
2-aryl cyclic 3-keto-1-en-1-ol herbicides (which includes herbicidal ester and carbonate derivatives of 2-aryl cyclic 3-keto-1-en-1-ols) (such as phenylpyrazole herbicides, preferably pinoxaden);
and combinations of any two of the aforementioned herbicides.

More preferred herbicides are selected from the group consisting of flucarbazone or propoxycarbazone or a salt (e.g. sodium salt) of either of these, mesosulfuron-methyl or a salt (e.g. sodium salt) thereof, iodosulfuron-methyl or a salt (e.g. sodium salt) thereof, bensulfuron-methyl or a salt (e.g. sodium salt) thereof, pyroxsulam or a salt (e.g. sodium salt) thereof, clodinafop, clodinafop-propargyl, fenoxaprop, fenoxaprop-P-ethyl, pinoxaden, and combinations of any two of the above herbicides. Still more preferred herbicides are selected from the group consisting of pyroxsulam or a salt (e.g. sodium salt) thereof, pinoxaden, clodinafop-propargyl, and combinations of any two of these herbicides. Most preferred herbicides are selected from the group consisting of pyroxsulam, pinoxaden, and clodinafop-propargyl.

The outcome of the process of the invention, namely the very high yield of carboxylic acid (IV) resulting from acid hydrolysis of ester (V) followed by treatment with base is unexpected, because acid hydrolysis of esters of carboxylic acids is generally known to be a reversible process.

Preferably, the particles of carboxylic acid (IV) have a $DV_{10}$ (i.e. 10% by volume of the population of particles fall below this size) in the range of between 1 and 15 µm (micrometers). More preferably, the $DV_{10}$ is between 5 and 10 µm (micrometers). Even more preferably, the $DV_{10}$ is between 7 and 8 µm (micrometers).

Preferably, the particles of carboxylic acid (IV) have a $DV_{50}$ (i.e. 50% by volume of the population of particles fall below this size) in the range of between 15 and 35 µm or between 15 and 36 µm (micrometers). More preferably, the $DV_{50}$ is between 20 and 30 µm (micrometers) or is between 24 and 36 µm. Even more preferably, the $DV_{50}$ is between 24 and 26 µm (micrometers).

Preferably, the particles of carboxylic acid (IV) have a $DV_{90}$ (i.e. 90% by volume of the population of particles fall below this size) in the range of between 35 and 70 µm (micrometers). More preferably, the $DV_{90}$ is between 40 and 60 µm (micrometers). Even more preferably, the $DV_{90}$ is between 42 and 47 µm (micrometers).

Preferably, the particles of carboxylic acid (IV) have a $DV_{10}$ in the range of between 1 and 15 µm (micrometers), a $DV_{50}$ in the range of between 15 and 35 µm (micrometers), and a $DV_{90}$ in the range of between 35 and 70 µm (micrometers). More preferably, the particles of carboxylic acid (IV)

have a $DV_{10}$ in the range of between 5 and 10 μm (micrometers), a $DV_{50}$ in the range of between 20 and 30 μm (micrometers), and a $DV_{90}$ in the range of between 40 and 60 μm (micrometers). More preferably, the particles of carboxylic acid (IV) have a $DV_{10}$ in the range of between 5 and 10 μm (micrometers), a $DV_{50}$ in the range of between 24 and 36 μm or between 24 and 26 μm (micrometers) and a $DV_{90}$ in the range of between 42 and 47 μm (micrometers).

Therefore, in a further (third) aspect, the invention relates to particulate carboxylic acid of formula (IV) having one or more of the above-defined particle size distributions.

Preferably, in all aspects of the invention, in the carboxylic acid (IV), $R_1$ is chlorine.

Therefore, a still further aspect of the invention (a preferred embodiment of the third aspect of the invention) provides a particulate carboxylic acid of formula (IVa):

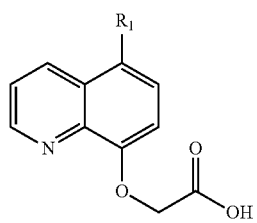

(IVa)

wherein $R_1$ is chlorine,
having a volume average particle size distribution such that $DV_{10}$ is in the range of between 1 and 15 micrometers, $DV_{50}$ is in the range of between 15 and 35 micrometers, and $DV_{90}$ is in the range of between 35 and 70 micrometers.

Preferably, the particulate carboxylic acid of formula (IVa), has a volume average particle size distribution such that $DV_{10}$ is between 5 and 10 micrometers, $DV_{50}$ is between 20 and 30 micrometers, and $DV_{90}$ is between 40 and 60 micrometers. More preferably, the particles of carboxylic acid (IVa) have a $DV_{10}$ in the range of between 5 and 10 micrometers, a $DV_{50}$ in the range of between 24 and 36 micrometers (e.g. between 24 and 26 micrometers) and a $DV_{90}$ in the range of between 42 and 47 micrometers.

Carboxylic acids (IV) or (IVa) having the particle size distribution of the invention are believed to offer advantages for formulation as pesticides, and in particular in solid, suspension or suspoemulsion formulations together with herbicides.

Another aspect of the invention provides a herbicidal composition comprising particulate carboxylic acid (IVa), as defined herein, together with at least one herbicide, and optionally one or more agriculturally acceptable carriers, adjuvants and/or excipients. Preferred herbicides can be as mentioned hereinabove. In this herbicidal composition, preferably, the herbicide is selected from pyroxsulam, pinoxaden, clodinafop-propargyl, and combinations thereof.

In general, particle sizes (D50, D10, D90, etc.) can be measured by sieving with one or more sieves. Suitable sieves include 53, 63, 75, 90, 106, 125, 150, 180, 212, 250, 300, 355, 425, 500, 600, 630, 710, 810, or 850 micron (μm) sieves, or 1.00, 1.18, 1.40, 1.60, 1.65, 1.70, 2.00, 2.36, 2.46, 2.80, 3.35, or 4.00 mm sieves.

Alternatively, particle sizes can be measured by laser diffraction, also known as low angled laser light scattering (LA-LLS). Laser diffraction is based on the angular distribution of scattered light. Laser diffraction is known to the skilled person and can use an algorithm based on a Fraunhoefer or Mie optical model also known to the skilled person. The technique may be conducted on the liquid suspension of the particles. Further details of the laser diffraction technique can be found in: Clive Wash., "Particle Size Analysis in Pharmaceutics and Other Industries, Theory and Practice", Ellis Horwood Limited, 1992, see in particular Chapter 6, p. 109-133, details of which are hereby incorporated by reference. The Fraunhoefer calculation is described therein and is commonly performed by the software analysis package provided as part of commercially available laser diffraction apparatus e.g. as now described. Suitable laser diffraction apparatus include (a) the Malvern Mastersizer S, obtainable from Malvern Instruments Limited, Enigma Business Park, Grovewood Road, Malvern, Worcestershire WR14 1XZ, United Kingdom, website: www.malvern.co.uk; and/or (b) the Sympatec HELOS/QUIXEL, obtainable from Sympatec UK and Ireland, Bury Business Centre, Kay Street, Bury BL9 6BU, United Kingdom, or the CILAS 920, available from CILAS 8, Avenue, Buffon, BP 6319, Orleans, Cedex-45063, France.

Particle size analysis methods typically assume sphericity of particles in the calculation of the distribution. In cases where non-spherical particles are analysed, skilled interpretation is required to understand the influence that shape may have on skewing the size distribution. Particle sizing techniques that utilise images of the particles such as microscopy can, however, accurately infer particle shape and size, though typically size would still be expressed assuming sphericity.

The invention is illustrated by the following non-limiting examples.

EXAMPLES

Example 1

Preparation of (RS)-1-methylhexyl (5-chloroquinolin-8-yloxy)acetate (cloquintocet-mexyl)

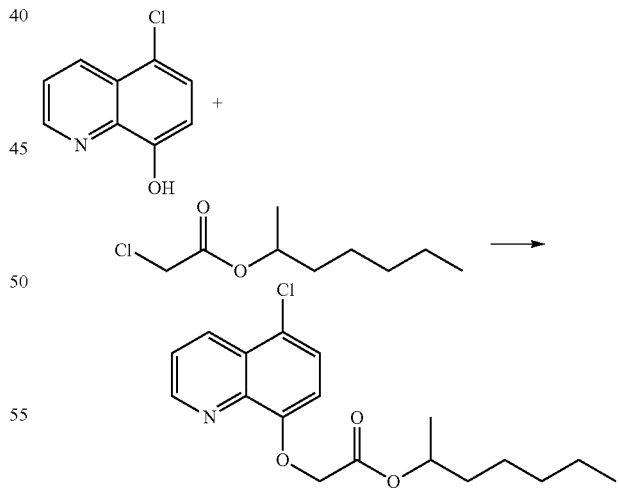

A solution 53.9 g (0.30 mol) of 5-chloro-2-hydroxyquinoline ("CHQ") in 136 g of NMP (N-methyl pyrolidinone) and 60 g of toluene was stirred at 45° C. in a 1 L jacketed vessel. A solution of sodium hydroxide (25%) (11.4 g, 0.285 mol) was added over 20 minutes. The temperature was raised to 85° C. and the water was removed under vacuum by azeotropic distillation. When all the water was removed, a further 35 g of toluene is distilled.

K$_2$CO$_3$ (4.15 g, 0.03 mol) was added to the reaction mixture, followed by the addition of chloro-acetic acid-1-methylhexyl ester 59.15 g (0.360 mol) over 1 hour. When the addition was complete, the temperature was raised to 95° C. and the reaction mixture is stirred for a further 3 hours. After control of the reaction completion the solvent was removed under vacuum to obtain the crude cloquintocet-mexyl as a melt.

Example 2

Preparation of (5-chloroquinolin-8-yloxy)acetic acid (cloquintocet acid)—Acidic Hydrolysis (Invention)

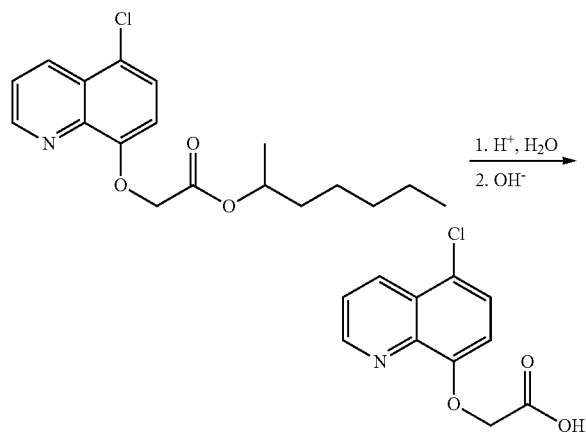

The melt from Example 1 was cooled to 90° C. and 415 g of demineralised water was added. Subsequently, 41.1 g (0.36 mol) of aqueous hydrochloric acid (32%) was added and the mixture heated under reflux. The 2-heptanol released during the hydrolysis was distilled off and separated using a Dean-Stark apparatus. After completion of the hydrolysis and complete removal of the 2-heptanol, a solution of 25% of sodium hydroxide (59.3 g) was added over a period of 2 hours maintaining the temperature at 90° C. until pH of 2.8 was reached. The resulting suspension was cooled to 20° C. and the solid filtered, washed with 2×50 mL of water and finally dried to provide 63.7 g of cloquintocet acid. (Titration by NaOH=95.4%). The filtration time was 15 seconds.

The cloquintocet acid obtained had the following particle size distribution, as measured by diffraction laser particle size analysis using a CILAS 920 particle size analyser, and using a suspension of the material in water. DV$_{10}$=7.37 µm; DV$_{50}$=24.52 µm; DV$_{90}$=44.63 µm. FIG. 1 shows the full particle size distribution obtained.

The addition of sodium hydroxide was repeated to a range of final values of pH. These results are shown in Table 1.

TABLE 1

| Final pH | Yield of cloquintocet acid (%) |
|---|---|
| 0.6 | 86.4 |
| 2.9 | 97.9 |
| 2.8 | 99.3 |

Example 3

Synthesis, Isolation of Identification of Cloquintocet Acid Hydrochloride, Starting from cloquintocet-mexyl

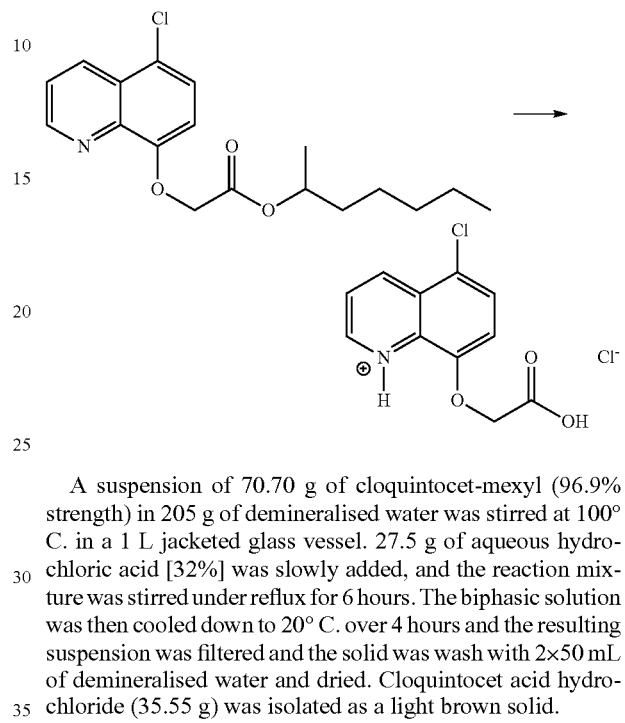

A suspension of 70.70 g of cloquintocet-mexyl (96.9% strength) in 205 g of demineralised water was stirred at 100° C. in a 1 L jacketed glass vessel. 27.5 g of aqueous hydrochloric acid [32%] was slowly added, and the reaction mixture was stirred under reflux for 6 hours. The biphasic solution was then cooled down to 20° C. over 4 hours and the resulting suspension was filtered and the solid was wash with 2×50 mL of demineralised water and dried. Cloquintocet acid hydrochloride (35.55 g) was isolated as a light brown solid.

Elemental analysis: C=48.7%, H=3.5%, N=5.2%, Cl=24.7%. Calculated: C=48.20%, H=3.31%, N=5.11%, Cl=25.87%.

Reference Example 4

Preparation of (5-chloroquinolin-8-yloxy)acetic acid (cloquintocet acid)—Acidic Hydrolysis (Comparison)

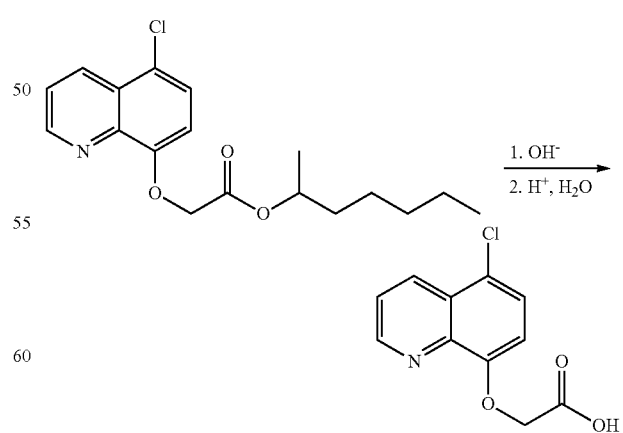

A suspension of 70.70 g of cloquintocet-mexyl (96.9% strength) in 220 g of demineralised water was stirred at 100° C. in a 1 L jacketed glass vessel. 39.2 g of a 25% solution of sodium hydroxide was slowly added, the heptanol formed during the hydrolysis was distilled off using a Dean-Stark apparatus. After completion of the reaction, hydrochloric acid was slowly added to the reaction mixture until pH of 2.8 was reached. The suspension was then cooled down to 20° C. over 4 hours and the resulting suspension was filtered and the solid washed with 2×50 mL of demineralised water and dried. Cloquintocet acid was isolated as a light brown solid. The filtration time was 25 seconds. The product strength (purity) was 94.5% weight/weight. It was difficult to completely solubilise the product acid after isolation because of the presence of insoluble impurities.

The invention claimed is:

1. A process for the preparation of a carboxylic acid of formula (IV)

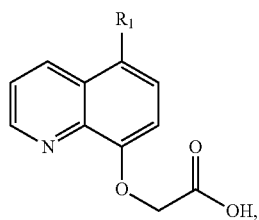

(IV)

wherein $R_1$ is hydrogen or chlorine,
comprising the steps of:
(i) subjecting a compound of formula (V)

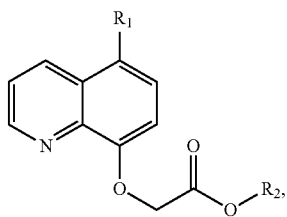

(V)

wherein: $R_1$ is as defined above; and $R_2$ is $C_1$-$C_{18}$alkyl; $C_1$-$C_6$alkoxy$C_1$-$C_8$alkyl-; or phenyl or benzyl, wherein the phenyl or benzyl is optionally substituted on the ring by 1, 2 or 3 of independently fluorine, chlorine, $C_1$-$C_2$alkyl, $C_1$-$C_2$alkoxy, $C_1$fluoroalkyl, or $C_1$fluoroalkoxy;
to hydrolysis under acidic conditions to give a solution of a quinolinium salt whose cation is of formula (VI)

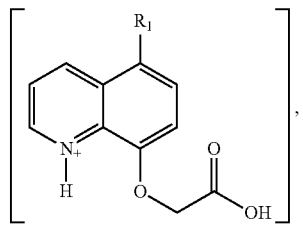

(VI)

wherein $R_1$ is as defined above; and
(ii) adding base to the solution obtained in step (i) to give the free carboxylic acid (IV).

2. A process as claimed in claim 1, wherein $R_1$ is chlorine.

3. A process as claimed in claim 1 wherein $R_2$ is straight-chain $C_1$-$C_{10}$ alkyl or non-tertiary branched $C_3$-$C_{10}$ alkyl.

4. A process as claimed in claim 1 wherein the acid hydrolysis step (i) is carried out under aqueous conditions and uses an acid having a p$K_a$ of less than 1.

5. A process as claimed in any preceding claim 1 wherein, in the hydrolysis step (i), the reaction is conducted at a temperature ranging from 50 to 120° C.

6. A process as claimed in claim 1 wherein, in step (ii), the base comprises a group (I) or group (II) metal hydroxide or carbonate.

7. A process as claimed in claim 1 wherein the base added in step (ii) is aqueous lithium hydroxide, aqueous sodium hydroxide or aqueous potassium hydroxide.

8. A process as claimed in claim 1 wherein the base in step (ii) is added until a pH in the range of 1.8 to 3.8 is achieved.

9. A process as claimed in claim 8 wherein the base in step (ii) is added until a pH in the range of 2.5 to 3.1 is achieved.

10. A process as claimed in claim 1 wherein $R_2$OH, which is produced in hydrolysis step (i) as a by-product, is continuously removed from the reaction mixture.

11. A process as claimed in claim 1 comprising the further step of combining compound (IV) with a herbicide and optionally one or more agriculturally acceptable carriers, adjuvants and/or excipients.

12. A process as claimed in claim 1 wherein the carboxylic acid (IV) obtained has a volume average particle size distribution such that $DV_{10}$ is in the range of between 1 and 15 micrometers, $DV_{50}$ is in the range of between 15 and 35 micrometers, and $DV_{90}$ is in the range of between 35 and 70 micrometers.

13. A compound of the formula

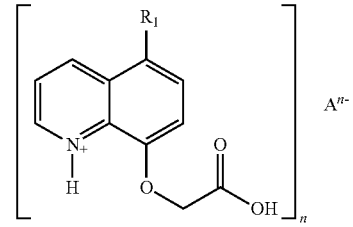

wherein n is 1, 2 or 3, $R_1$ is as defined in claim 1, and $A^{n-}$ is an n valent anion.

14. Particulate carboxylic acid of formula (IVa):

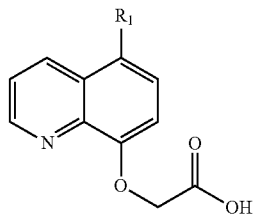

(IVa)

wherein $R_1$ is chlorine,
having a volume average particle size distribution such that $DV_{10}$ is in the range of between 1 and 15 micrometers, $DV_{50}$ is in the range of between 15 and 35 micrometers, and $DV_{90}$ is in the range of between 35 and 70 micrometers.

15. Particulate carboxylic acid of formula (IVa), as claimed in claim 14, having a volume average particle size distribution such that $DV_{10}$ is between 5 and 10 micrometers, $DV_{50}$ is between 20 and 30 micrometers, and $DV_{90}$ is between 40 and 60 micrometers.

16. A herbicidal composition comprising particulate carboxylic acid (IVa), as defined in claim 14, together with at least one herbicide, and optionally one or more agriculturally acceptable carriers, adjuvants and/or excipients.

17. A herbicidal composition as claimed in claim 16, wherein the herbicide is selected from pyroxsulam, pinoxaden, clodinafop-propargyl, and combinations thereof.

* * * * *